United States Patent [19]

Finn et al.

[11] 4,061,585

[45] Dec. 6, 1977

[54] METHOD OF USING HETEROPOLYSACCHARIDES PRODUCED BY THE FERMENTATION OF METHANOL

[75] Inventors: Robert K. Finn; Alex L. Tannahill, both of Ithaca, N.Y.; Joseph E. Laptewicz, Jr., Groton, Conn.

[73] Assignee: Cornell Research Foundation, Inc., Ithaca, N.Y.

[21] Appl. No.: 746,595

[22] Filed: Dec. 1, 1976

Related U.S. Application Data

[62] Division of Ser. No. 592,603, July 2, 1975, Pat. No. 4,016,865, which is a division of Ser. No. 523,559, Nov. 14, 1974, Pat. No. 3,932,218, which is a division of Ser. No. 364,559, May 29, 1973, Pat. No. 3,923,782.

[51] Int. Cl.² .......................... C11D 3/22; H01M 4/20; B01J 13/00
[52] U.S. Cl. ..................... 252/89 R; 137/13; 210/51; 252/309; 252/311; 252/DIG. 15
[58] Field of Search ............... 252/89, DIG. 15, 309, 252/311; 210/51; 137/13

[56] References Cited

U.S. PATENT DOCUMENTS

| | | | |
|---|---|---|---|
| 3,208,526 | 9/1965 | Patton et al. | 166/38 |
| 3,230,919 | 1/1966 | Crawford | 114/67 |
| 3,414,512 | 12/1968 | Johnson | 210/51 |
| 3,520,313 | 7/1970 | Seymour | 137/13 |
| 3,679,582 | 7/1972 | Wagenaar et al. | 252/8.3 |
| 3,729,460 | 4/1973 | Patton | 260/209 R |

*Primary Examiner*—P.E. Willis, Jr.
*Attorney, Agent, or Firm*—Lawrence E. Laubscher; Ralph R. Barnard; Theodore C. Wood

[57] ABSTRACT

Disclosed is a new heteropolysaccharide polymer and a method for producing this polymer by a fermentation process comprising culturing a heteropolysaccharide-producing strain of a micro-organism of the genus Methylomonas on an aqueous culture medium containing methanol as the sole source of assimilable carbon. Several uses for the heteropolysaccharide are also disclosed such as its use as a drag reducing agent, a thickening agent, an emulsifier, a soil suspending agent and a flocculant or deflocculant.

5 Claims, 4 Drawing Figures

METHOD OF USING HETEROPOLYSACCHARIDES PRODUCED BY THE FERMENTATION OF METHANOL

This is a division of application Ser. No. 592,603 filed July 2, 1975, now U.S. Pat. No. 4,016,865, which in turn is a division of application Ser. No. 523,559 filed Nov. 14, 1974, now U.S. Pat. No. 3,932,218 which in turn is a division of Ser. No. 364,559, filed May 29, 1973, now U.S. Pat. No. 3,923,782.

BACKGROUND OF THE INVENTION

The present invention relates to the production of biopolymers and more especially to the preparation of polysaccharides by fermentation using methanol as the sole source of assimilable carbon. The invention also relates to the use of these biopolymers as drag reducing agents, as thickening agents, emulsifiers, soil suspending agents, flocculants or deflocculants, etc.

Biopolymers have recently been the subject of increased research studies because of the interesting properties exhibited by such polymers and the various applications suggested by these properties. The polysaccharides which have been studied most are those produced by fermentation utilizing bacteria of the genus Xanthomonas which generally utilize carbohydrates as the source of assimilable carbon in a culture medium. These biopolymers act as versatile thickening agents for aqueous acids, alkalis and brines, and are good suspending agents for solids-in-water and oil-in-water dispersions, and act also as excellent rheology control agents. Thus, the xanthan gums find application in oil well drilling mud systems, as additives for secondary recovery of petroleum by water flooding, and as stabilizers, emulsifiers and thickeners in food products.

In view of economic considerations, however, it would be more desirable to employ petrochemicals as the source of assimilable carbon in fermentation systems rather than carbohydrates. Of petrochemicals, methane or methanol would be the most economical. Some studies have been made on bacteria utilizing these compounds as a carbon source. For example, Leadbetter and Foster (*Archiv fur Mikrobiologie*, 30, 91–118, 1958) isolated and grew several cultures of pseudomonads in a mineral salts medium with methane as the sole source of carbon and energy. Harrington and Kallio (*Can. J. Microbiol.*, 6, 1–7, 1960) have published work on the oxidation of methanol by *Pseudomonas methanica*. But despite the numerous studies on the specific activities of methane- and methanol-utilizing bacteria and theorization as to the metabolic pathways, very little work has been conducted regarding characterization of the biopolymers formed or in investigating the properties and utilities of these products resulting from fermentation in culture media containing methane or methanol.

One factor prompting investigation of the properties of the biopolymers according to the present invention is that inexpensive conventional polymeric materials utilized in dilute aqueous solutions to produce a drag-reducing effect, such as polyethylene oxides and polyacrylamides, suffer from certain drawbacks. For example, these polymers are relatively unstable to salt and acid or alkaline conditions, and they tend to breakdown in molecular weight during flow as a result of turbulent conditions and moderate shearing forces. These disadvantageous factors are also present in many of the polymeric thickening agents presently being employed in drilling muds and flooding agents for secondary recovery of oil in the petroleum industry.

SUMMARY OF THE INVENTION

It is an object of the present invention to provide a process for the production of heteropolysaccharides through the fermentation of bacteria in a culture medium utilizing methanol as the sole source of carbon.

It is another object of this invention to provide a new polysaccharide having desirable properties.

Still another object of the invention resides in the production of an improved drag-reducing agent for use in dilute aqueous systems.

It is also an object of the present invention to provide an improved thickening agent suitable for use in foods, cosmetics, paints, drilling muds, and especially in flooding composition utilized in the secondary recovery of underground petroleum deposits.

A further object of the present invention is to provide a polysaccharide displaying improved properties for use as an emulsifier, a flocculent or defloculent and a soil suspending agent.

In accomplishing the foregoing objects, there has been provided according to the present invention a method for producing a heteropolysaccharide by fermentation which comprises culturing a heteropolysaccharide-producing strain of a microorganism of the genus Methylomonas on a culture medium containing methanol as the sole source of assimilable carbon. The crude, cell-free polysaccharide, as precipitated by acetone from the fermentation broth, contains from about 60 to 90% by weight organic matter and from about 10 to 40% ash. Most of the latter consists of phosphates (15 to 25%) and cations (5 to 25%). The constituent sugars of the polymer are glucose (10 to 30%), galactose (3 to 15%) and mannose (3 to 15%) and the polymer contains a significant amount of pyruvic acid (5 to 35%). The crude polymer is negatively charged and a 1% solution has a viscosity of 300–400 centipoise (Brookfield viscometer at 30 rpm). Fermentation is carried out at a pH between about 6.0 and 7.8 and preferably within the range of 6.2 to 7.5, and at a temperature between 25° C. and 33° C. The heteropolysaccharide produced by this process exhibits excellent thickening and drag-reducing properties when employed in dilute aqueous solutions and is particularly stable to salts, acids, bases and to mechanical shear forces. The polymer finds many uses not only as a drag-reducing agent, but also as a thickening agent in foods, cosmetics, paints, drilling muds, and especially in flooding compositions utilized for the secondary recovery of underground petroleum deposits.

DETAILED DESCRIPTION OF THE INVENTION

Figure 1:
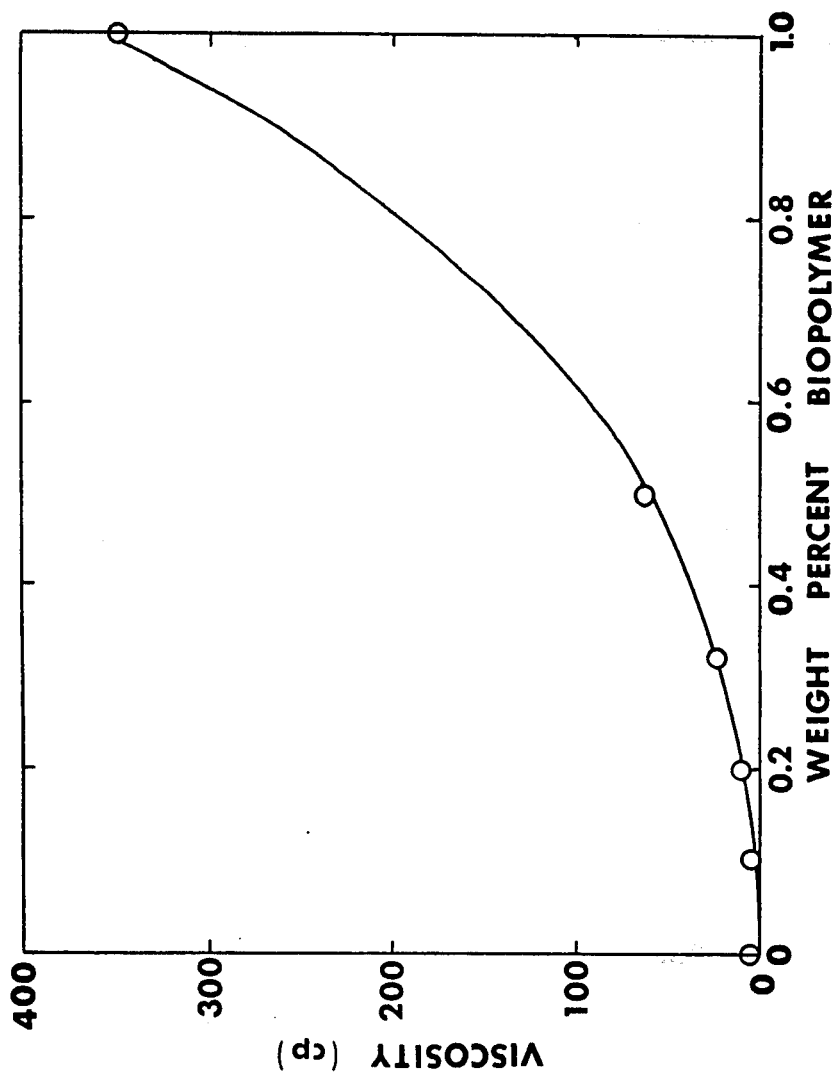
FIG. 1 is a graphical plot of viscosity correlated with the weight percent of biopolymer in aqueous solution.

The microorganisms employed in accordance with the present invention are of the type isolated by Tannahill and Finn from soil samples ("Fermentation Process Based on Methanol", Paper presented to the 160th National ACS Meeting, Chicago, Sept. 7, 1970). A specimen of this particular isolate has been deposited with the Northern Regional Research Laboratory of the U.S. Department of Agriculture in Peoria, Illinois, and is identified by the number NRRL B-5695. A sample of this microorganism can be obtained from the aforementioned Research Laboratory. (The deposit was made with the understanding that all restrictions on the availability to the public being irrevocably removed upon the granting of a patent.) Its mycological characteristics are presented in detail below:

A. Morphological observations
 1. Salts-methanol (3% methanol) agar slant, 24 hours, vegitative cells, straight rods, 0.2-0.4 × 1.0-2.0 microns, singly or in pairs, motile by single polar flagellum, no spore formation, gram negative.

B. Cultural characteristics
 1. Salts-methanol (3% methanol) agar colonies - 2 days, moderate to abundant growth, circular, pulvinate, smooth, glistening, entire, mucoid, yellow, medium unchanged.
 2. Salts-methanol (3% methanol) agar streak - 2 days, moderate to abundant growth, filiform, smooth, glistening, bright yellow, butyrous to mucoid, medium unchanged.
 3. Pigment does not diffuse into the medium.

C. Physiological characteristics
 1. Relation to free oxygen: strictly aerobic, pellicle formed in broth tubes, surface growth in agar stabs.
 2. Temperature: optimum growth temperature, 28°-30° C.; growth at 10° C.; no growth at 35° C.
 3. pH for growth: optimum pH, 6.7 to 7.2; pH limits for growth 6.0 to 7.8.
 4. Catalase: positive (method of Skerman).
 5. Gelatine hydrolysis: weakly positive after 24 hours (key gelatin strips).
 6. Oxidase: positive (Key oxidase test tablets).
 7. Pectinesterase: positive (method of McComb).
 8. Nitrate reductase: positive (method of Skerman).
 9. Growth in presence of 1% sodium chloride, but no growth with 2% sodium chloride.
 10. Utilization of other carbon sources: no growth was detected utilizing methane, formaldehyde, formamide, formate, ethanol, methylamine, glycine, DL-serine, succinate, D-glucose, fructose, glycerin or oxalate after a period of 48 hours had elapsed.
 11. Litmus milk: no reaction.
 12. No growth on nutrient agar, but no inhibition of growth if methanol added to the nutrient agar.
 13. Absorption spectrum of the carotinoid pigment is similar to that of Psuedomonas methanica.
 14. Yeast extracts and other vitamin mixtures do not stimulate growth.
 15. Ammonium salts, nitrates, or urea serve as nitrogen sources. Other organic nitrogen sources can probably be used also.

D. Source: soil

E. Cell free extracts contained little HDP activity, but contained appreciable HPS activity according to the method of Kemp and Quayle. This suggests metabolism of methanol by the allulose pathway rather than the serine pathway.

The isolate of Tannahill and Finn exhibits certain similarities to the strain identified as *Pseudomonas methanica* by Dworkin and Foster (J. Bact., 72, 646, 1956) but it is noted that differences exist: the isolate is not as phosphate sensitive, grows within a much narrower pH range, does not grow on methane, and is more stable, i.e. does not exhibit the color variability reported for the known organism. No pink or colorless variants of the isolate have been noted.

On the basis of the foregoing, it is concluded that the microorganism of Tannahill and Finn belongs to the genus Methylomonas, which has been defined by Ribbons et al (Annual Review of Microbiology, vol. 24, pp. 135-158, 1970) as follows:
 1. Obligate methylotroph;
 2. motile with polar flagellation;
 3. rod shaped; and
 4. forming only immature cyst.

The present organism, since it does not fall within any previously described species, has been designated as *Methylomonas mucosa*.

The broth medium utilized for growth of the microorganism consists of the following:

| Material | Grams per Liter |
|---|---|
| $KH_2PO_4$ | 3.75 |
| $Na_2HPO_4$ | 2.50 |
| $(NH_4)_2SO_4$ | 2.00 |
| $MgSO_4 \cdot 7H_2O$ | 0.40 |
| $Ca(NO_3)_2 \cdot 4H_2O$ | 0.025 |
| $FeSO_4 \cdot 7H_2O$ | 0.005 |
| $ZnSO_4 \cdot H_2O$ | 0.005 |

This corresponds to the "minimal salts" formulations, except that in the preferred embodiment a slightly higher concentration of calcium ions is employed because it has been found that an increase in calcium ions stimulates growth. Ammonium sulfate was the nitrogen source used for most of the work with this organism; however, it is also possible to utilize sodium nitrate and likewise obtain excellent growth. It was found that the organism can tolerate a methanol concentration of up to about 7.0% by volume. The optimum growth occurred, however, with methanol concentrations between about 0.5 and 5.0% by volume, whereas the most preferred concentration is between about 2.0 and 3.0%. Similarly, it was determined that the pH value of the medium greatly effected growth, with no growth taking place below a pH of 5.7 to above a pH of 8.0. Accordingly, a pH range of from about 6.0 to about 7.8 is suitable for growth of this microorganism, although a reasonable growth rate occurs only within the range of about 6.2 to about 7.5. Optimal growth takes place at a pH of approximately 7.0.

The cultivation procedure involves adding the salts to water in the above listed order followed by pasteurization or autoclaving if desired. It is not absolutely essential that the culture medium be sterilized prior to introduction of the microorganism since the organism is able to grow at such high methanol levels that there is not much competition from other organisms. This is a distinct advantage as regards several of the particular use applications for which these microorganisms are especially suited. Moreover, the property makes it possible to operate the fermentation process as a continuous process. Methanol is then added to the salt solution at approximately room temperature. When solid media is desired to carry the organism, 1.75% Bacto Agar may be added to the salts before pasteurization or autoclaving. Growth is carried out preferably at about 30° C. in a shaker-incubator (controlled environmental incubator shaker, New Brunswick Scientific Company, Incorporated) utilizing one liter shaker flasks filled with from about 200 to 400 milliliters of broth. Growth times are normally from about 48 to 96 hours. After this period a highly viscous slime has been produced in the culture broth.

Recovery of the fermentation produce may be accomplished in conventional ways utilizing acetone, methanol, propanol, quaternary ammonium salts, etc. as precipitants. Use of acetone has proven to be most appropriate according to the present invention. Accordingly, the broth culture can be first centrifuged for a period of from 10 to 20 minutes to remove some of the bacterial cells, and the clarified, slightly yellow supernatant decanted from the centrifuge to leave a cell pellet behind. To this supernatant is added from 1.2 to 2.0 parts by volume of acetone, preferably 1.5 parts, per part of supernatant, and the mixture is well mixed. The biopolymer is obtained as a light-colored cottony precipitate. It is then drained, placed into from 2 to 3 parts of fresh acetone to remove as much water as possible, and finally dried at room or elevated temperature to give a dry, powdery product. The average yield of polymer after 48 hours, based on methanol used is about 40 percent. About 20 to 25% of the methanol is converted to cell mass.

To determine the chemical identity of the biopolymer, a variety of tests were performed. By running a UV spectrum (Perkin Elmer No. 202 Spectrophotometer) on the cell-free sample, it is determined that the biopolymer contains no protein or nucleic acids since there are no peaks at 280nm or 260nm. The tests for polybeta-hydroxybutyric acid is negative (method of Law and Slepecky). The iodine test (method of Daniel and Neal) indicates that the polymer is not starch or glycogen, whereas an ash test discloses that 39.4% of the crude polymer is inorganic. An infra-red spectrum suggests the presence of phosphate groups, carboxyl groups and possibly amine groups among the sugar molecules. The anthrone method for total carbohydrate shows the polymer to contain from 18 to 22% carbohydrate, and the Nelson method indicates a content of reducing substances of 20%. Finally, all of the polymer is precipitated from solution by the addition of a cationic detergent, cetyl trimethylammonium bromide. A table summarizing these results is presented below.

TABLE 1

| | Assay | Result |
|---|---|---|
| (1) | UV Spectrum | No protein or nucleic acids |
| (2) | Polybeta-hydroxybuteric acid | Negative test |
| (3) | Iodine test | Not starch or glycogen |
| (4) | Ash test | 39.4% inorganic content |
| (5) | IR spectrum | Presence of phosphate, carboxyl and amine groups suggested |
| (6) | Anthrone test | 18 to 22% carboyhydrate (based on glucose); cationic detergent polymer is negatively charged and precipitates completely |

An elemental analysis performed on the biopolymer, twice reprecipitated, gives the following results:

TABLE 2

| Element | Per Cent By Weight |
|---|---|
| P | 6.24 |
| Ca | 0.144 |
| K | 12.00 |
| Mg | 0.600 |
| Na | 3.500 |
| N | 2.00 |
| | Concentration ppm |
| Zn | 356.0 |
| Mn | 9.6 |
| Fe | 77.6 |
| Cu | 15.2 |
| B | 5.6 |
| Al | 135.2 |

After acid hydrolysis, gas chromatographic analysis of the constituent sugars showed the following molar ratios: glycose 9 – 10; galactose 5 – 6; mannose 4 – 5.

Some of the physical properties of the biopolymer were studied, for example, solutions of the polymer were measured for viscosity at 25° C. under a variety of conditions. The measurements of viscosity were made with a Brookfield viscometer at 30 r.p.m. in all cases. A curve showing viscosity (in centipoise) as a function of weight percent polymer is presented in FIG. 1.

Figure 2:
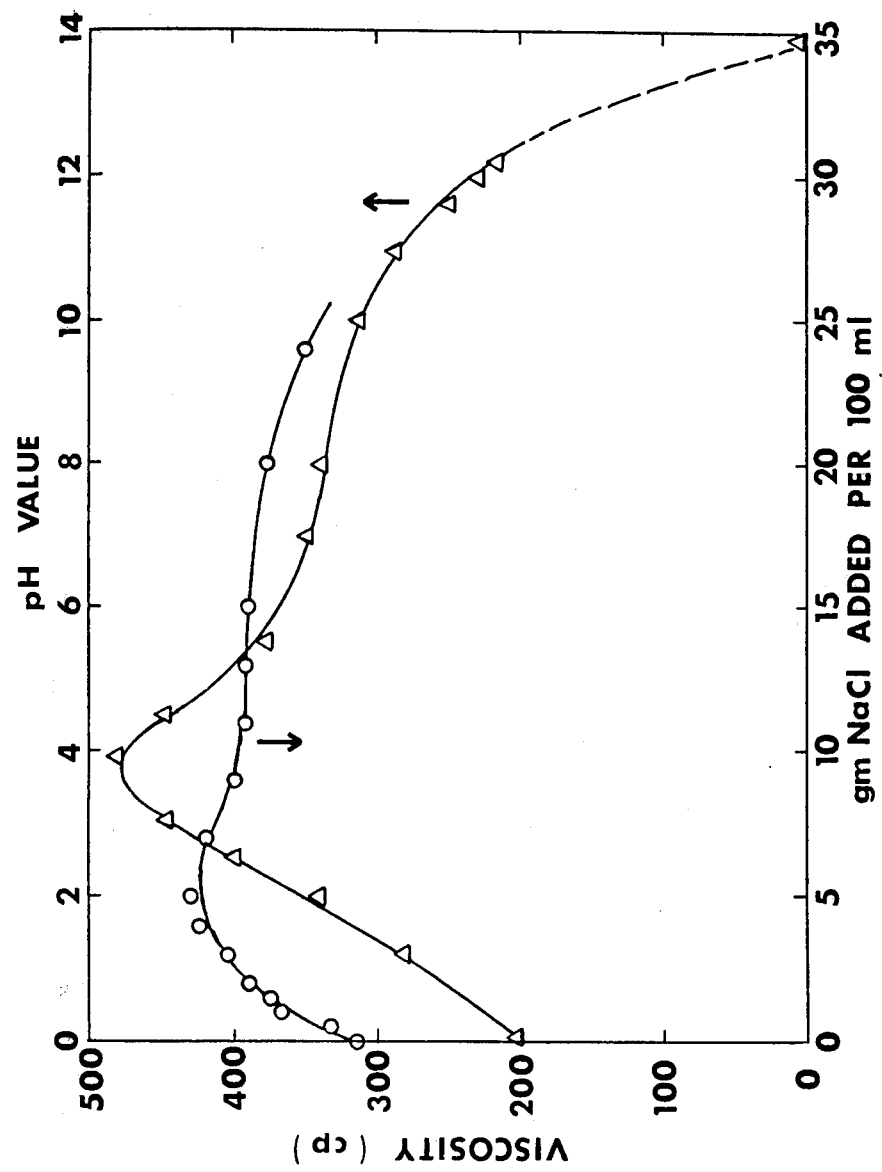
FIG. 2 illustrates graphically the relationship between the viscosity of an aqueous solution of polymer and both salt concentration and pH.

The intrinsic viscosity of the polymer in five percent sodium chloride was 14.8 deciliters per gram, which indicates a fibrous rather than globular macromolecule of molecular weight in the range one to five million. The effect of sodium chloride concentration on the viscosity of a solution of polymer was tested by adding dry sodium chloride to a 1% solution of redissolved acetone-precipitated polymer. The curve in FIG. 2 illustrates that the viscosity was stable over a wide range of salt concentrations, a factor of significant importance in certain of the utility applications contemplated for the present biopolymer. Also, in FIG. 2 is shown the effect of pH on solution viscosity. These data were obtained by the addition of potassium hydroxide or sulfuric acid to adjust the pH of 1.0% solutions of polymer in water. It can be seen that the viscosity rose from pH 7.0 to a maximum at pH 4.0, then declined as the pH was lowered further. The viscosity gradually declined as the pH was raised above 7.0. The addition of 10% sulfuric acid did not hydrolyze the polymer in solution whereas the addition of 10% potassium hydroxide did.

Figure 3:
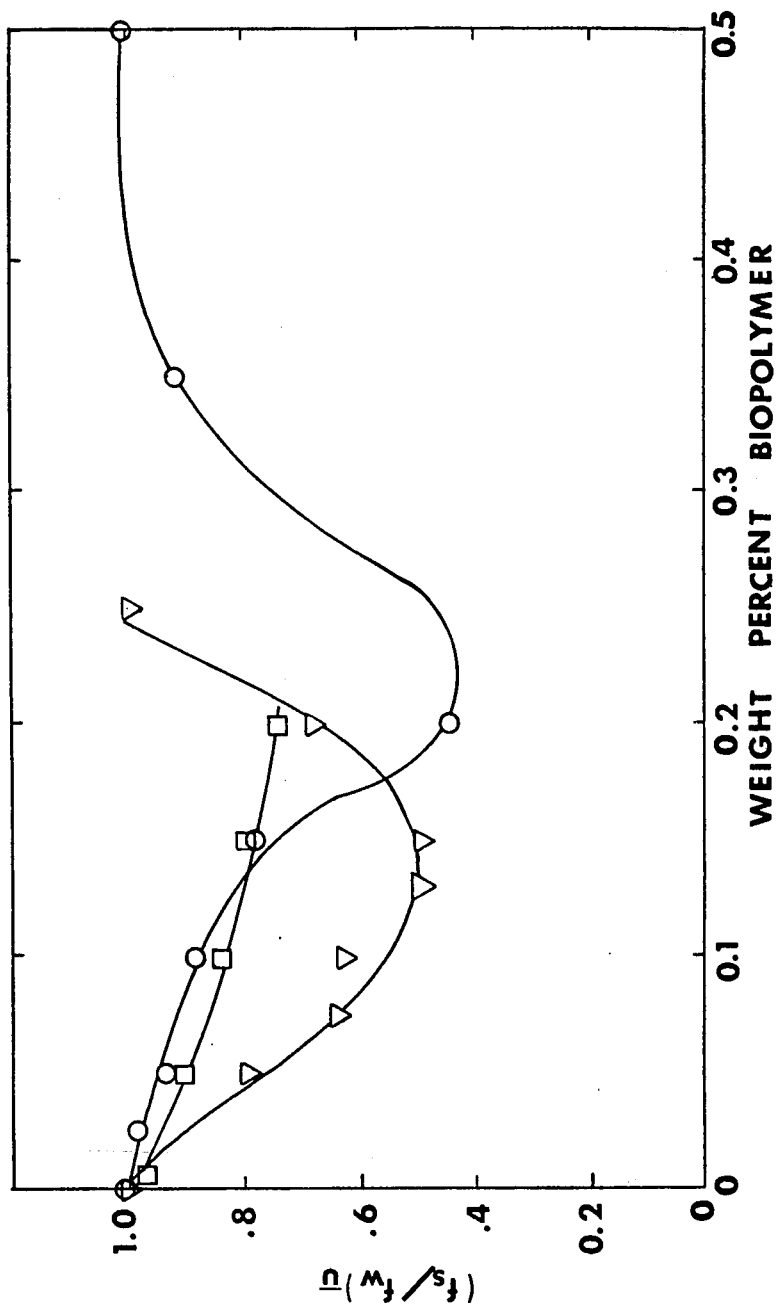
FIG. 3 is a graph showing the drag-reducing properties of the biopolymers of the invention in relation to their concentration in aqueous solution; triangles represent a crude polymer containing cells, circles represent a membrane-filtered, cell-free solution.

The biopolymer according to the present invention were found to produce a very interesting drag reduction phenomenon. Drag reduction experiments were conducted on solutions of the biopolymer utilizing the technique described by Rodriguez in Engineering Education (to be published, 1973). The parameters adopted for the apparatus were as follows: reservoir height = 4 feet, horizontal tube diameter = 0.29 cm., length of horizontal tube = 59 cm., vertical distance of effluent point to measuring point = 6 inches. In FIG. 3 is illustrated the reduction in the friction factor of the polymeric solution as a function of weight percent cell-free polymer at 30° C. Experiments were also conducted to verify the fact that the drag reduction occurred due to a true solution of polymer and not due to particulates.

Figure 4:
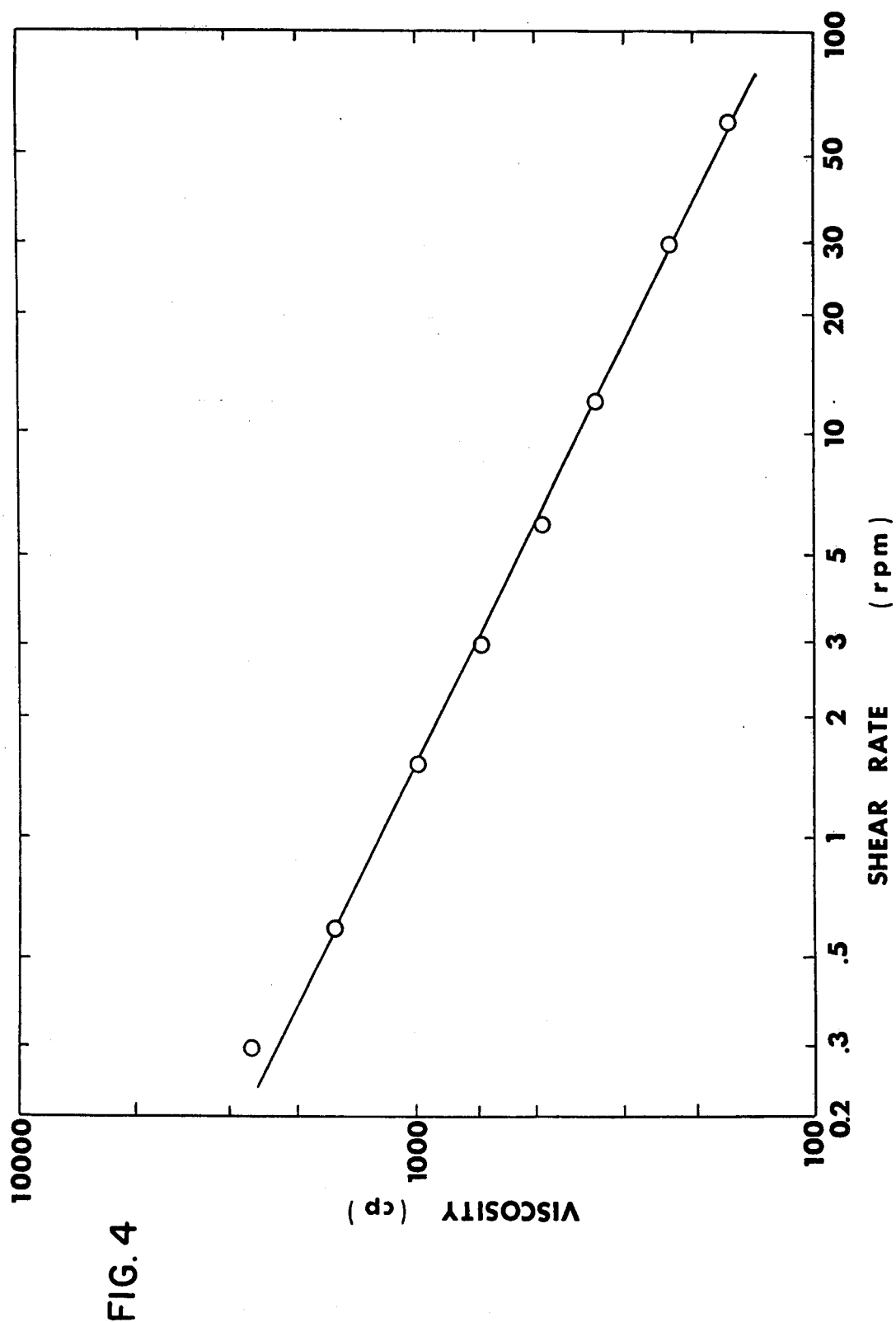
FIG. 4 is a graphical plot of viscosity in relation to shear rate.

The biopolymer according to the present invention was found to be comparable in its drag reducing capability to the more conventionally employed polyethylene oxide and polyacrylamide polymers and also to other organic materials displaying drag-reducing properties, such as carrageenan. Because of the cheapness and ready availability of methanol, which constitutes the sole source of carbon for the present biopolymers, there results a significant economic advantage to utilizing the polymers of the present invention as drag-reducing agents as well as in other utilities. Moreover, whereas polyethylene oxide is subject to breakdown in molecular weight during flow due to turbulent conditions and therefore tends to degrade after one or two passes through a pipe flow system, the biopolymers of the present invention have been found to be highly resistant to such shear degradation. Thus, a solution of the present polymer was passed through the test apparatus 15 times and no degradation was observed. Exposure of a drag-reducing solution of the instant polymer in a Waring blender for a period of 2 minutes degraded the biopolymer, as would be expected, and the reduction in the solution's friction factor was decreased significantly. FIG. 4 illustrates the non-Newtonian property illustrated by a solution (10 gm/l.) of the crude polymer.

The biopolymers of the invention have been found to be particularly useful in several types of applications. For example, as a result of their exhibition of drag-reducing properties in dilute aqueous solutions, they are particularly suited for use in fire fighting equipment to enable propulsion of a stream of water over longer distances, for addition to storm sewer systems in periods of heavy water loads, for application to nautical vessels to assist in increasing speed through the water, for improvement of the operation of papermaking processes and for use in general in recirculating aqueous systems. Typically, the polymers are employed in an aqueous solution in a concentration of from about 0.02 to about 0.20 grams per liter.

The biopolymers of the present invention are also useful as thickening agents. In addition to finding utility as thickeners in conventional applications such as in foods, cosmetics, paints and the like, the present biopolymers have proved to be particularly well suited for various drilling field applications in the petroleum industry. For example, an excellent drilling mud is obtained when the mucopolysaccharide is employed as a thickener in an amount of from about 0.05 to about 3.0 percent by weight of the composition. Moreover, because the biopolymers of the present invention are anionic polymers and because they maintain their viscosity in the presence of sodium chloride, they are particularly well suited for use in flooding compositions employed in the secondary recovery of petroleum products in subterranean cavities. Also, because the fermentation process utilized in the preparation of these biopolymers employs only an aqueous solution of inorganic salts plus methanol, it is relatively insensitive to the competition of other microorganisms, and further, because methanol concentrations can be made as high as 3–5% at which level most other organisms are inhibited, the present polymers lend themselves ideally to preparation directly in the drilling field, a location which is also typically close to an inexpensive supply of methanol. A typical flooding composition may contain between about 0.01 percent and about 1.0 percent by weight of the heteropolysaccharide of the invention. The polysaccharides of the present invention are employed in accordance with conventional principles, and for further information regarding the use of biopolymers in the aforementioned utilities, reference may be had to U.S. Pat. No. 3,020,207, No. 3,243,000 and No. 3,406,114. The present biopolymer is also useful as an emulsifier, flocculent or deflocculent, and as a soil suspending agent.

The following examples are included to more clearly illustrate the invention, it being understood that the same are merely intended to be illustrative and not in any sense limitative.

EXAMPLE 1

350 milliliters of a culture broth having the following composition are sterilized for 20 minutes at 120° C.:

| Material | Grams Per Liter |
| --- | --- |
| $KH_2PO_4$ | 3.75 |
| $Na_2HPO_4$ | 2.50 |
| $(NH_4)_2SO_4$ | 2.00 |
| $MgSO_4 \cdot 7H_2O$ | 0.40 |
| $Ca(NO_3)_2 \cdot 4H_2O$ | 0.025 |
| $FeSO_4 \cdot 7H_2O$ | 0.005 |
| $ZnSO_4 \cdot H_2O$ | 0.005 |

The above was mixed with 3% by volume of methanol, inoculated with the strain *Methylomonas mucosa* and was cultivated with shaking at 30° C. for 72 hours. The pH is metered constantly and appropriate amounts of KOH or $H_2SO_4$ are added to maintain the pH at 7.0.

At the end of the fermentation time, the broth culture is centrifuged at 20,000 g. for 15 minutes to remove some of the bacterial cells. Then acetone is added in an amount of 1.5 volumes per volume of broth supernatant obtained by decanting the clear, slightly yellow liquid from the centrifuge tube, leaving the cell pellet behind. The acetone-broth combination is mixed well and cell-free polymer is recovered as a light-colored cottony precipitate. The polymer is drained, then placed into 2 parts of fresh acetone to remove as much water as possible, and is finally dried at room temperature for 24 hours. 3.2 grams of the crude solid polymer are obtained having an analysis as follows:

1. Organic matter 62.6%
   a. glucose 10.7%
   b. mannose 4.1%
   c. galactose 5.2%
   pyruvic acid 16.0%
   e. unidentifiables 26.6%
2. Inorganic matter 37.4%
   a. phosphates 19.1%
   b. cations 18.3%

EXAMPLE 2

The dispersant action of the biopolymer is demonstrated in a test wherein 0.2 gms ZnO powder suspended in 250 ml of distilled water was allowed to settle in a graduated cylinder. After 30 minutes the upper layer (5 ml sample) was tested for light transmission (Bausch and Lomb, Spectronic 20 meter).

|  | Optical Density Reading |
| --- | --- |
| No addition of biopolymer | 0.24 |
| With 1 part biopolymer per 100 parts ZnO | 0.28 |
| With 2 parts biopolymer per 100 parts ZnO | 0.40 |

While the present invention has been described hereinabove with reference to several specific embodiments thereof, it is readily apparent that minor modifications, alterations and substitutions may be made in the processes of preparing and using the subject heteropolysaccharide polymer without departing from the spirit of the present invention. Therefore, it is intended that the invention be limited only by the scope of the claims appended hereto.

We claim:

1. A method of dispersing insoluble powders in aqueous media, comprising adding to said aqueous media an heteropolysaccharide of bacterial origin having an intrinsic viscosity in the range of about 10 to 20 deciliters per gram and comprising the following constituents on a weight percent basis:
   1. Organic matter of 60% to 90% comprising
      a. 10% to 30% glucose;
      b. 3% to 15% mannose;
      c. 3% to 15% galactose; and
      d. 5% to 35% pyruvic acid;
   2. Inorganic matter of 10% to 40% comprising
      a. 5% to 25% phosphates; and
      b. 5% to 25% cations;

said polysaccharide being added in an amount of from 1:500 to 1:20 parts by weight of polysaccharide to parts by weight of suspended solids.

2. A method of flocculating an aqueous suspension of particulate solids, comprising adding an heteropolysaccharide of bacterial origin having an intrinsic viscosity in the range of about 10 to 20 deciliters per gram and comprising the following constituents on a weight percent basis:
   1. Organic matter of 60% to 90% comprising
      a. 10% to 30% glucose;
      b. 3% to 15% mannose;
      c. 3% to 15% galactose; and
      d. 5% to 35% pyruvic acid;
   2. Inorganic matter of 10% to 40% comprising
      a. 5% to 25% phosphates; and
      b. 5% to 25% cations;

said polysaccharide being added in an amount of from about 1:100 to 1:5 parts by weight of polysaccharide to parts by weight of suspended solids.

3. A method of reducing frictional drag in the pumping of water or dilute aqueous solutions, comprising incorporating into the aqueous composition from about 0.05 to 0.3 percent by weight of an heteropolysaccharide of bacterial origin having an intrinsic viscosity in the range of about 10 to 20 deciliters per gram and comprising the following constituents on a weight percent basis:
   1. Organic matter of 60% to 90% comprising
      a. 10% to 30% glucose;
      b. 3% to 15% mannose;
      c. 3% to 15% galactose; and
      d. 5% to 35% pyruvic acid;
   2. Inorganic matter of 10% to 40% comprising
      a. 5% to 25% phosphates; and
      b. 5% to 25% cations.

4. A method of emulsifying oils into an aqueous phase, comprising adding to the aqueous phase from about .05 to 0.5 percent by weight of an heteropolysaccharide of bacterial origin having an intrinsic viscosity in the range of about 10 to 20 deciliters per gram and comprising the following constituents on a weight percent basis:
   1. Organic matter of 60% to 90% comprising
      a. 10% to 30% glucose;
      b. 3% to 15% mannose;
      c. 3% to 15% galactose; and
      d. 5% to 35% pyruvic acid;
   2. Inorganic matter of 10% to 40% comprising
      a. 5% to 25% phosphates; and
      b. 5% to 25% cations.

5. A method of preventing soil redeposition in detergent formulations, comprising adding to said formulations from about .01 to 0.1 percent by weight of an heteropolysaccharide of bacterial origin having an intrinsic viscosity in the range of about 10 to 20 deciliters per gram and comprising the following constituents on a weight percent basis:
   1. Organic matter of 60% to 90% comprising
      a. 10% to 30% glucose;
      b. 3% to 15% mannose;
      c. 3% to 15% galactose; and
      d. 5% to 35% pyruvic acid;
   2. Inorganic matter of 10% to 40% comprising
      a. 5% to 25% phosphates; and
      b. 5% to 25% cations.

* * * * *